United States Patent [19]  [11] 4,224,695
Grundei et al.  [45] Sep. 30, 1980

[54] ENDOPROSTHETIC ELBOW JOINTS

[75] Inventors: Hans Grundei; Joachim Henssge; Gerhard Schütt, all of Lübeck, Fed. Rep. of Germany

[73] Assignee: Schütt & Grundei GmbH, Lübeck, Fed. Rep. of Germany

[21] Appl. No.: 15,966

[22] Filed: Feb. 28, 1979

[30] Foreign Application Priority Data

Mar. 16, 1978 [DE] Fed. Rep. of Germany ....... 2811331

[51] Int. Cl.³ .............................................. A61F 1/03
[52] U.S. Cl. .................... 3/1.91; 128/92 C
[58] Field of Search ........................ 3/1.91; 128/92 C

[56] References Cited

U.S. PATENT DOCUMENTS

| 3,919,725 | 11/1975 | Swanson et al. | 3/1.91 |
| 4,038,704 | 8/1977 | Ring | 3/1.91 |
| 4,057,858 | 11/1977 | Helfet | 3/1.91 |
| 4,079,469 | 3/1978 | Wadsworth | 3/1.91 |
| 4,129,902 | 12/1978 | Harmon | 3/1.91 |

FOREIGN PATENT DOCUMENTS 1444724 8/1976 United Kingdom ..................... 3/1.91

Primary Examiner—Clifford D. Crowder
Attorney, Agent, or Firm—Balogh, Osann, Krammer, Dvorak, Genova & Traub

[57] ABSTRACT

An endoprosthetic elbow joint in the form of a one-piece endoprosthesis having at least one hinge joint provided with anchoring shanks of which one is to be connected to the humerus and of which the other is to be connected to the ulna of a patient, the axis of the hinge joint taking the place of the flexing and extending axis of the natural arm. According to the invention, the end of the hinge joint on the side on which the patient's radius will be situated continues into a rotary humeroradial joint which is rigidly connected to the hinge joint. The rotary joint has at least two degrees of freedom, one of which allows pivoting movement of the joint by a shank thereof for anchoring in the radius about the flexing and extending axis of the hinge joint and of which the other allows rotary movement by the shank about the longitudinal axis of the patient's radius. Advantageously, the rotary joint has a further degree of freedom which allows axial movement by the shank of the rotary joint along the longitudinal axis of the patient's radius.

7 Claims, 7 Drawing Figures

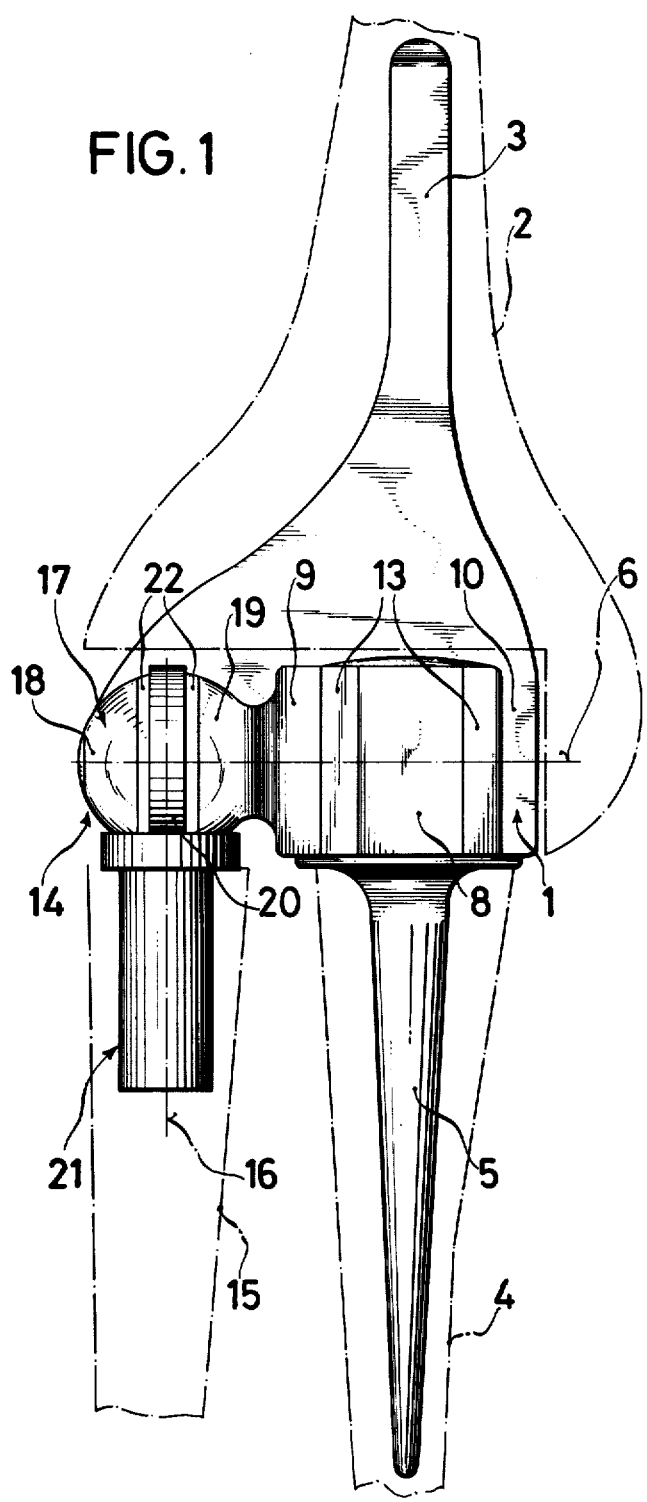
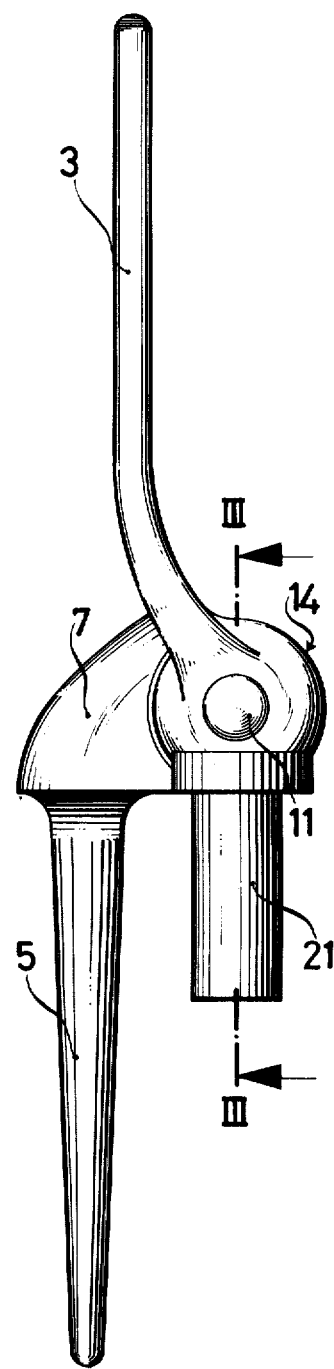

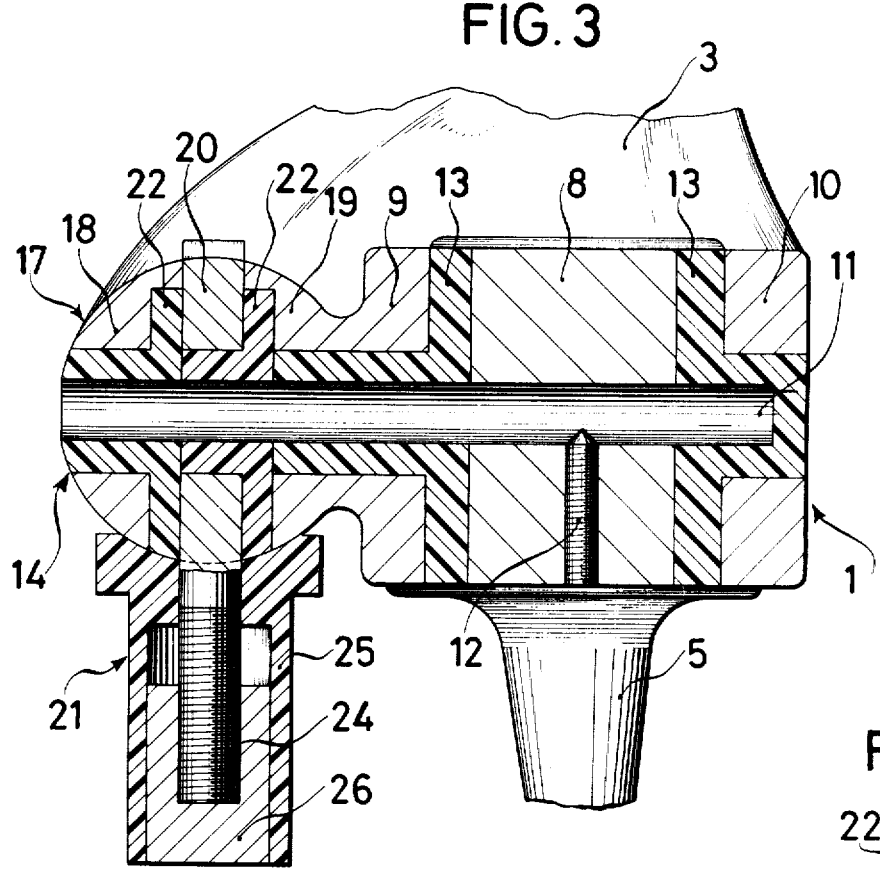
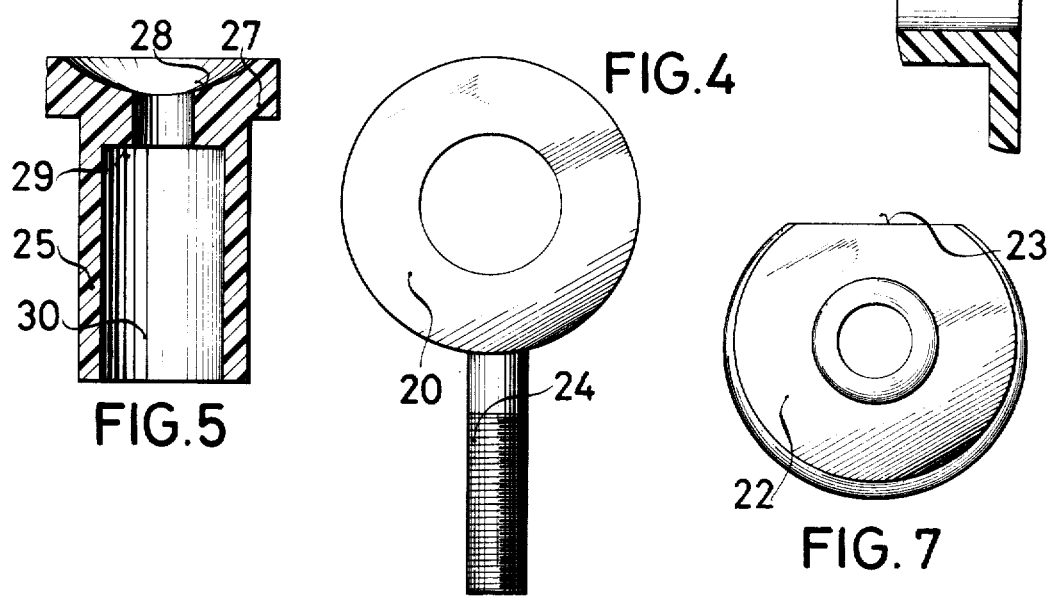

ENDOPROSTHETIC ELBOW JOINTS

BACKGROUND OF THE INVENTION

The present invention relates to endoprosthetic elbow joints in the form of a whole endoprosthesis having at least one hinge joint provided with anchoring shanks of which one is to be connected to the humerus and the other of which is to be connected to the ulna of a patient, the axis of the hinge joint taking the place of the flexing and extending axis of the natural arm. Hereinafter such joints will be referred to as "of the kind described".

Endoprosthetic elbow joints of the kind described are not complete replacements for the natural elbow joint since they do not have a part which performs the function of the humeroradial articulation in the elbow region. Existing artificial elbow joints are constructed simply on the principle of a hinge-joint and have one shank to be anchored in the humerus and one shank to be anchored in the ulna, these two bones of the arm having removed from them the damaged parts or parts which would hamper the fitting of the artificial joint before the joint is in fact fitted. An operation on the joint has to be performed and in it the damaged parts of the humeroradial articulation are removed and are either not replaced or else are replaced by parts which are not connected to the hinge joint and which provide only a minimum of the mobility and load bearing capacity of the natural arm. However, in comparison with the natural joint, the overall load bearing capacity of an arm fitted with an artificial joint of this kind falls far short of expectations, in particular as regards the taking up and transmission of pressure or reaction forces acting on the hand, due to the fact that an appropriate proportion of the forces cannot be transmitted via the radius because the relevant part of the joint is missing or inadequate for the purpose.

It is an object of the invention to provide an elbow joint of the kind described in which the radius of the arm retains its ability to transmit pressure forces at the same time as its natural mobility in rotation is preserved.

SUMMARY OF THE INVENTION

Accordingly, the invention consists in an endoprosthetic elbow joint of the kind described, wherein the end of the hinge joint on the side on which the radius is situated continues into a rotary humeroradial joint which is rigidly connected to said hinge joint, and said rotary joint has at least two degrees of freedom, one of which allows pivoting movement of said rotary joint by a shank thereof for anchoring in the radius about the flexing and extending axis of said hinge joint and of which the other allows rotary movement by said shank about the longitudinal axis of the patient's radius.

With a joint according to the invention, it becomes possible for the radius to perform its natural function again, the joint, when implanted, causing no pain to the person concerned when loads are applied. Since the radius has a secure connection to the artificial joint no matter what position the joint is in, it is able to transmit virtually the same proportion of the pressure and reaction forces mentioned as it would naturally, without any danger that it will be dislodged from the joint. This is true both when the arm is in any bent position and also when the forearm is rotated, so that the mobility of the forearm in rotation, under load and without pain, is also restored to it.

Advantageously, the rotary humeroradial joint has a simple mechanical connection to the radius to allow both flexion and extension and also rotation of the forearm. The elbow joint according to the invention is in addition comparatively simple and inexpensive to produce and also presents no extra-normal problems at the time of implanting. It is also designed in such a way that there is substantially no frictional wear which could lead to irritation in the joint.

BRIEF DESCRIPTION OF THE DRAWINGS

Other objects and advantages of the invention will become apparent from the following description taken in conjunction with the accompanying drawings which show one embodiment thereof by way of example and in which:

FIG. 1 is an elevation view of an elbow joint according to the invention with the bones of the patient's arm indicated in chain lines, FIG. 2 is a side view of the joint shown in FIG. 1, FIG. 3 is a sectional view to an enlarged scale on line III—III of FIG. 2 to show the individual parts of the joint more clearly, FIGS. 4 to 6 show individual parts of the new joint, and FIG. 7 is a front view of the individual part which is shown in section in FIG. 6.

DETAILED DESCRIPTION OF THE PREFERRED EMBODIMENT

Referring now to the drawings, as shown in FIGS. 1 and 2, an elbow joint in the form of a whole endoprosthesis to replace the natural human elbow joint, comprises firstly a simple, hinge joint 1 known per se, having a shank 3 which is to be inserted in the patient's humerus 2 and anchored solidly in place there and a shank 5 which is to be anchored in the patient's ulna 4. The axis of pivot 6 of the hinge joint 1 takes the place of the natural flexing and extending axis of the human arm. The joint is in addition so constructed that it cannot be pivoted beyond the fully extended position of the natural arm, for which purpose part 7 of the shank 5 comes to bear in a suitable known fashion against the humeral shank 3 of the joint.

Through central mounting bores located in the mounting part 8 of the ulnar shank 5 and the two lateral mounting parts 9 and 10 of the humeral shank 3 extends a hinge pin 11 which defines the hinge axis 6 and connects the shanks together, as can be seen in precise detail in FIG. 3. The point of a threaded pin 12 which screws into the central mounting part 8 engages in the suitably prepared hinge pin 11 in order to lock the latter relative to the mounting part 8 and thus avoid frictional wear and also in order to secure it axially. As can also best be seen in FIG. 3, disc-shaped inserts 13 of plastics material, preferably polyethylene, with tubular extensions are provided between mounting parts 8, 9 and 10 and hinge pin 11 in order to prevent frictional wear between the said parts, which generally leads to irritation in the joint. For this reason, one of the inserts 13 is also formed to be sealed off on the outside and both the inserts are secured against rotation, e.g. by means of flats on their circumference, which flats bear against corresponding contact faces belonging to the mounting parts 9 and 10.

The side view in FIG. 2 shows the position and arrangement of the shanks 3 and 5 of the hinge joint 1 relative to the hinge pin 11.

In accordance with a principal feature of the invention, the end of the joint 1 on the side on which the radius is situated continues into a further, rotary joint 14 which is intended to provide a connection between the radius 15 of the forearm and the humerus 2, doing so in such a way that the natural mobility of the human forearm and its ability to transmit forces are largely preserved. Accordingly, the rotary humeroradial joint has at least two degrees of freedom, that is to say a first degree of freedom about the pivot axis 6 already mentioned conforming to the natural flexing and extending axis of the arm, and secondly a degree of freedom about the axis of articulation 16 of the radius 15, with axis 16 intersecting axis 6.

In an advantageous refinement of the rotary humeroradial joint 14 of the elbow joint according to the invention which, in the case shown in FIG. 1, is a joint for a human right arm, the rotary joint 14 comprises specifically a spherical mating region 17 with lateral mounting parts 18 and 19 which are integral with the humeral shank 3, and a central mounting part 20 which is mounted between the lateral mounting parts to pivot about the axis 6 and which is connected to a further shank 21 which may be formed integrally for anchoring in radius 15 (as shown in FIGS. 1 and 2). As can be seen in FIG. 3, the mounting bores in these parts line up with the mounting bores in the hinge joint 1, so that the hinge pin 11 of the latter, if extended, can also act as a connecting member for the rotary humeroradial joint 14. Once again provided in the present case are disc-shaped inserts 22 of plastics material, preferably polyethylene, which are provided with tubular extensions, to prevent frictional wear as the joint operates. The arrangement of these inserts is clearly evident in FIG. 3.

The inserts 22 are of course mounted in such a way as not to rotate, like the similar inserts 13. FIGS. 6 and 7 show the outer insert 22 of the rotary joint 14, FIG. 7 showing that the insert is prevented from rotating by a flat 23 on its circumference, when this flat bears against a corresponding forming in the mounting parts 18 and 19.

To connect it to the joint shank 21, mounting part 20 has a threaded spigot 24 which extends axially into a sleeve 25 also composed of a suitable plastics material, particularly polyethylene, which is to be anchored in the radius 15 (but at the same time being rotatably mounted—rotatable with radius 15—with respect to spigot 24), the threaded spigot 24 being held in the bore in the sleeve by means of a coaxial threaded socket 26 which is screwed onto the threaded spigot 24. The threaded socket 26 has a cylindrical outer surface which rests against the inside wall of the radius sleeve 25, allowing the radius sleeve to freely rotate about the longitudinal axis of the radius, and ensuring that the radius sleeve and thus the radius 15 are securely mounted. Also, at the end nearer the joint or upper end, the radius sleeve 25 has a flange 27 which is provided with a concave joint cavity 28, the surface of which slides on the surface of the spherical mating region 17 of the rotary joint 14.

Although the rotary joint 14 is still capable of operating if the threaded socket 26 is screwed onto the threaded spigot 24 until it bears axially against the radius sleeve 25, it is also possible for a certain amount of axial clearance to be left, as can be seen in FIG. 3. The threaded socket 26 is then shortened by an appropriate amount so that it can bear against the internal shoulder 29 in the stepped internal bore 30 in the radius sleeve 25 should the radius sleeve draw away from the spherical mating region. This creates an abutment which restricts the axial movement of the radius under load. Alternatively, it is possible for the shoulder to be entirely dispensed with, if in this way the bearing area of the joint cavity 28 can be made sufficiently large to transmit a reaction force and if the natural ligaments are able to prevent the radius sleeve from drawing away from the mating region 17. This opportunity for axial movement by the sleeve 25 represents a third degree of freedom for the rotary joint 14.

The mating region 17 of the rotary humeroradial joint 14 has been described above as completely spherical. It is of course adequate for the proportion of it which is of a spherical configuration to be merely that necessary to allow the natural flexion and extension of the arm to take place over the requisite angular range and to afford the possibility of rotary movement, since the joint cavity 28 of the joint shank 21 slides only on the part of the mating region in question.

An essential feature of the embodiment described above is that there is a mechanical connection between the mating region 17 of the rotary joint 14 and the joint shank 21 namely via the central mounting part 20 having the threaded spigot 24. In an alternative form of the rotary joint 14 according to the invention, it is possible for there to be no such mechanical connection. The mating region 17 is then in the form of a one-piece ball or a body of this nature part of which has a surface of spherical curvature covering the natural angular range over which the arm is flexed and extended. The shank 21 to be anchored in the radius 15 is then a solid body which merely carries the joint cavity 28, the latter sliding on the spherically curved mating surface of the mating region 17 and being pressed against this surface by the natural ligaments. A design of this kind for the rotary joint 14 is possible in applications where the natural ligaments are completely undamaged and sufficiently strong to hold together a rotary joint so formed.

Apart from the components of the joint which are composed of plastics material, its other components are composed of the metallic or ceramic materials which are normally used in the art for replacement joints.

We claim:

1. In an elbow joint in the form of an endoprosthesis having at least one hinge joint provided with anchoring shanks of which one is to be connected to the humerus and the other is to be connected to the ulna of a patient, and a hinge pin which connects the shanks together and defines the axis thereof, the hinge joint having a central mounting bore extending through its mounting parts for receiving said hinge pin, the axis of the hinge joint taking the place of the flexing and extending axis of the natural arm, the improvement which comprises a rotary humeroradial joint connected to the hinge joint on the side thereof on which the patient's radius is situated, said rotary humeroradial joint being connected on its hinge side to the humeral section of the hinge joint and being provided with a spigot-like connecting member, on the side thereof adjacent the patient's radius, and a sleeve to be anchored in the radius and rotatably mounted therein with respect to said connecting member for engaging the latter and thereby transmitting forces from the radius to said rotary humeroradial joint, said rotary humeroradial joint having in its mating region, at least on the side adjacent the radius, a spherical surface which covers the angular range of flexible movement of the patient's natural arm, and the upper end of said radius sleeve being provided with a joint cavity, the surface of which slides on said spherical surface as a mating surface, whereby said rotary humeroradial joint has at least two degrees of freedom, one of which allows pivoting movement of said rotary humeroradial joint by a radius shank thereof about the flexing and extending axis of the hinge joint, and of which the other allows rotary movement by said radius shank about the longitudinal axis of the patient's radius, and a further degree of freedom which allows axial movement by said radius shank along the longitudinal axis of the patient's radius.

2. A joint according to claim 1, wherein said mating region of said rotary joint is of spherical configuration and comprises two fixed lateral mounting parts, which are connected to said humeral shank of the hinge joint, and a movable central mounting part which can pivot between them about said flexing and extending axis and which carries said connecting member for connection to the patient's radius, said mounting parts having each a central mounting bore lining up with the central mounting bore of the hinge joint, and wherein the hinge pin of the hinge joint is extended to allow it also to act as a hinge pin for said rotary joint.

3. A joint according to claim 2, wherein abrasion-resistant inserts are provided between said lateral mounting parts of said rotary joint on the one hand and between said mounting parts and said hinge pin on the other hand, and are arranged to be non-rotatable.

4. A joint according to claim 3, wherein the connecting member of said movable central mounting part of said rotary joint comprises a threaded spigot and a threaded socket with a cylindrical outer surface which is screwed onto said spigot, said threaded socket being mounted coaxially in said radius sleeve so that said radius sleeve is free to rotate about the longitudinal axis of said patient's radius.

5. A joint according to claim 4, wherein said radius sleeve has a stepped bore of which the larger-diameter section is situated to be adjacent the patient's radius and receives said threaded socket and said threaded spigot is screwed into it to allow a certain amount of axial travel, said stepped bore having shoulders acting as an abutment for said threaded socket.

6. A joint according to claim 2 wherein, at the end adjacent the joint, said radius sleeve has a flange which is provided with a concave joint cavity which bears against said spherical mating region of said rotary joint.

7. A joint according to claim 1, wherein an integrally formed shank is to be anchored in the patient's radius and said integrally formed shank has a concave joint cavity by which said integrally formed shank bears loosely against a spherically curved surface on the other part of said rotary joint, which is connected to said hinge joint.

* * * * *